US006602527B1

(12) United States Patent
Slaga et al.

(10) Patent No.: US 6,602,527 B1
(45) Date of Patent: Aug. 5, 2003

(54) PROCESSING METHOD FOR MANUFACTURING BLACK TEA AND AN IMPROVED BLACK TEA

(76) Inventors: Thomas J. Slaga, 1600 Pierce St., Lakewood, CO (US) 80214; Jifu Zhao, 1600 Pierce St., Lakewood, CO (US) 80214

( * ) Notice: Subject to any disclaimer, the term of this patent is extended or adjusted under 35 U.S.C. 154(b) by 0 days.

(21) Appl. No.: 09/721,438

(22) Filed: Nov. 22, 2000

(51) Int. Cl.[7] .............................. A23F 3/00; A23F 3/06; A23F 3/14

(52) U.S. Cl. ........................................ 426/49; 426/597

(58) Field of Search .................................. 426/597, 49

(56) References Cited

U.S. PATENT DOCUMENTS 6,113,965 A * 9/2000 Goodsall et al.
6,348,224 B1 * 2/2002 Patil et al.

OTHER PUBLICATIONS

Calzyme Laboritories Inc. Online Website Catalog. 1998 (http;//www.calzyme.com:80/catalog/tyrosina.html).*

* cited by examiner

Primary Examiner—Anthony J. Weier
(74) Attorney, Agent, or Firm—David G. Henry

(57) ABSTRACT

Fresh tea leaves or green tea are converted to black tea using tyrosinase oxidation which alters catechines (a group of green tea polyphenols) to theaflavins. Theaflavins are unique black tea polyphenols and a potential anti-sunburn and chemopreventive agents. The oxidation reaction is performed on leaves which contain moisture only in an amount that the oxidation reaction occurs under the conditions of temperature of 20–50° C., air or $O_2$ (0.2 to 2 moles $O_2$/kg dry tea) supply and pH 5.0 to 7.5 at localized sites on and within the tea leaf structure. The moisture is supplied by moistening fresh tea leaves or dry green tea to a limited degree with a proper amount and concentration of monophenol, catechol and polyphenol oxidases, and tyrosinase, or their combinations. Obtained black tea contains much more theaflavins than regular black tea, and is, therefore, a more healthful beverage than that produced through use of conventionally processed black tea.

6 Claims, No Drawings

PROCESSING METHOD FOR MANUFACTURING BLACK TEA AND AN IMPROVED BLACK TEA

BACKGROUND OF THE INVENTION

1. Field of the Invention

The present invention relates to the processing of tea leaves to produce black tea.

2. Background Information

The present invention relates to oxidation of green tea leaves to black tea. As is accepted in the art, green tea is tea which has been freshly picked and which generally has undergone treatment, such as a heat treatment, to inactivate enzymes contained in the tea which oxidize chemical substances contained in the tea.

Black tea is prepared conventionally by subjecting freshly picked tea leaves to various processing steps which include a fermentation step which employs enzymes naturally present in the tea to effect enzymatic oxidation of chemical substances contained in the tea which results in providing the organoleptic and aesthetic characteristics, i.e., aroma, flavor and color, associated with aqueous beverage extracts obtained from black tea. Extracts of black tea may be consumed as a hot beverage or may be chilled to provide a cold beverage, or the extracts may be processed further to provide an instant water-soluble product for preparation of hot and cold beverages.

Although beverages prepared from green and Oolong teas are appreciated by consumers in various parts of the world, in some localities, particularly in the United States, consumer preferences dictate that tea beverages have the organoleptic and aesthetic characteristics of beverage extracts obtained from black tea. In contrast to the distinctive reddish coloration of extracts obtained from black tea, aqueous extracts obtained from green tea, in particular, have a yellow-greenish coloration which tends to reinforce a perception in consumers that the extracts have a "grassy" flavor and aroma and a "bitter" taste. Oolong teas have organoleptic and aesthetic characteristics which fall in between those of green and black teas.

Seltzer discloses a process said to enable obtaining fermented black tea and partially fermented tea of more uniform quality from green tea. To obtain this objective, the process is carried out by extracting green tea leaves with water and then combining the aqueous extract with what is described as a "relatively small amount" of 'bruised' fresh tea leaves and then heating the mixture of the extract and bruised leaves in the presence of oxygen at a temperature not to exceed 43° C. for a period of time after which the reaction mixture is heated to inactivate the enzymes. The extract obtained is said to have characteristics of black tea.

Gurkin discloses treating an aqueous extract of green tea in the presence of oxygen or treating green tea leaf in the presence of water and oxygen at a temperature above 50° C., and preferably, at a temperature of from 75° C. to 125° C., under a pressure of at least 100 psig (7.03 kg/cm.sup.2), and preferably at a pressure of from 14.06 kg/cm.sup.2 to 56.24 kg/cm.sup.2. Times of treatment may range from 2 mins to 30 mins. It is taught that, preferably, the pH of the reaction media be above a pH of 7 prior to the treatment. In addition to demonstrating the effects of variables of pressure, time, pH and concentration of tea solids when treating aqueous extracts, Gurkin discloses treating macerated leaves in water in a ratio of water to leaf of 9:1. Gurkin also posits that the treatment may be carried out by adding a "small amount" of water to the green leaf and converting it to black tea leaf under the disclosed conditions.

Moore, which was assigned commonly with Seltzer and Gurkin, also discloses a process for treating water-soluble constituents of green tea leaves, particularly aqueous extracts thereof, in the manner of Gurkin. Moore, however, differs from Gurkin in that the process requires that the reaction media have a pH of at least 7.5. It is disclosed that such a pH was found to be a "major" factor affecting the color of the final product and that such a pH is necessary to produce a "practical degree of conversion within a commercially feasible time". When leaves are to be treated, Moore teaches that they are to be treated in an alkaline solution in which the majority of the solution is absorbed by the leaf.

SUMMARY OF THE INVENTION

It is an object of the present invention to provide an improved black tea manufacturing process through the use of the product of which produces a beverage of enhanced therapeutic or health enhancement qualities.

It is an object of the present invention to provide an improved black tea manufacturing process through the use of the product of which produces a beverage which elevated, beneficial theaflavins, when compared with beverages made from conventionally prepared black tea.

DETAILED DESCRIPTION OF THE PREFERRED EMBODIMENT

Mushroom tyrosinase rapidly reacts with dioxygen and then release oxygen and become deoxytyrosinase by oxidation of phenols or polyphenols. In fact tyrosinase is a catalyst in oxidation of phenols.

The present invention is characterized in that polyphenolic substances contained in moist fresh tea leaves having a moisture content of at least 20% by weight based upon the dry weight of tea solids contained in the moist leaves ("by weight dry tea solids") are oxidized at about 20–50° C. by spraying tyrosinase solution on them. For dry green tea, tyrosinase solution is used to soak the leaves. The oxidation duration is 10 to 360 minutes at a good air flow environment or supplying oxygen.

The reaction is characterized further in that the moist leaves are contacted with tyrosinase and molecular oxygen sufficient to the moist leaves to oxidize polyphenolic substances contained in the moist leaves. The treated leaves may be processed immediately for drying to obtain black tea, or preparing water-soluble instant tea products, or they may be dried for subsequent extraction for preparation of a beverage.

It has been discovered that the amount of moisture employed in the oxidizing treatment of the present invention is a very critical variable. By reason of the amount of moisture employed in the process of the present invention, the leaves to be treated are only moist which is believed to facilitate the permeation of the leaves by the oxidizing agent. Thus, in the process of the present invention, by reason of the leaves being only moist and thereby having almost no free water present, the oxidation reaction takes place in localized sites on and within the tea leaf structure. Therefore, the pH changes which occur due to the oxidation reaction occur substantially only at the localized sites and do not substantially affect neighboring oxidation reaction sites, which would occur if free water were present.

In carrying out the process of the present invention, the moist tea leaves, and hence the various oxidizable substances of the tea leaves, are contacted with molecular oxygen. Although various oxidizing agents can be employed to provide the molecular oxygen for the reaction, various chemical agents such as hydrogen peroxide or permanganate, for example, may be deemed undesirable because residues of the same in the treated leaves may be considered to be food additives, and thus, the final product therefore would not be considered to be 100% tea. Thus, gaseous oxidizing agents are most preferred.

Suitable gaseous oxidizing agents include ozone or ozone-containing gases, but more advantageously, an oxygen-containing gas, including air and oxygen enriched air may be employed. For most efficient results, however, oxygen gas is employed as the oxidizing agent.

When the tea leaves to be treated in accordance with the present invention are in a dry state, having a stable moisture content which conventionally is in a range of from about 5% to about 7% by weight dry tea solids, the leaves first are moistened with water solution of tyrosinase, conveniently in the vessel in which the oxidation step is to be performed. The moistening step should produce moisture contents no greater than approximately 40% by weight of dry tea solids. Higher levels of moisture should be avoided since such levels generally will result in saturation of the leaves and the presence of free water, the latter adversely affecting the quality of the oxidation reaction as discussed elsewhere herein.

The object of the moistening step is to moisten the leaves uniformly, and to that end, preferably, the leaves are moistened by spraying them with water by means such as with a series of nozzles contained in the vessel. Preferably, the leaves being moistened are agitated, such as with a stirrer, by tumbling, or by a fluidized bed, or other such agitating means. It would be preferred that the moist leaves and molecular oxygen be contacted in a countercurrent flow. For best results, after adding water solution of enzymes to the leaves, the moisture is allowed to equilibrate throughout the leaves, preferably while agitating the leaves, so that the moisture is substantially uniformly imbibed by and distributed in the leaves and so that there is no free water between and amongst the moist leaves to be treated in the oxidizing step.

EXAMPLES

The following examples are illustrative of the present invention and parts and percentages are by dry weight unless otherwise indicated. Theaflavins were quantified by HPLC and using standard theaflavins from SIGMA Company. Tyrosinase from SIGMA is composed of monophenol oxidase, polyphenol oxidase, catechol oxidase and oxidoreductase. It should be noted that these examples are only that —examples —a wide range of conditions, such as time and units of enzyme, can be used because more time in process will offset a lesser enzyme presence, and vice versa.

Example I

About 0.35 kg of a sample from a batch of dry Chinese green tea leaves are moistened in a vessel to a moisture content of about 25% by weight dry tea solids by spraying them with mushroom tyrosinase (SIGMA, 500,000 units) solution (pH 6.5) while agitating them. After adding the tyrosinase, agitation is continued for enabling the moisture to equilibrate throughout the leaves under the room temperature for 60 minutes. While agitating the moist leaves in the vessel, air is introduced into the vessel. Upon finishing the reaction, tea leaves were dried to get new black tea I.

An infusion extract obtained from the treated leaves for preparing a 0.1% by weight extract. It is found that the new black tea I contains 9% of theaflavins which are much higher than average black tea with about 1–4% of theaflavins.

Example II

About 0.5 kg of a sample from a batch of dry Chinese green tea leaves are moistened in a vessel to a moisture content of about 30% by weight dry tea solids by spraying them with mushroom tyrosinase (SIGMA, 500,000 units) solution (pH 6.5) while agitating them. After adding the tyrosinase, agitation is continued for enabling the moisture to equilibrate throughout the leaves under the room temperature for 90 minutes. While agitating the moist leaves in the vessel, air is introduced into the vessel.

Upon finishing the reaction, tea leaves were dried to get new black tea II. An infusion extract obtained from the treated leaves for preparing a 0.1% by weight extract. It is found that the new black tea II contains 12% of theaflavins.

Example III

About 0.2 kg of a sample from a batch of dry Chinese green tea leaves are moistened in a vessel to a moisture content of about 25% by weight dry tea solids by spraying them with mushroom tyrosinase (SIGMA, 250,000 units) solution (pH 5.5) while agitating them. After adding the tyrosinase, agitation is continued for enabling the moisture to equilibrate throughout the leaves under the room temperature for 30 minutes. While agitating the moist leaves in the vessel, air is introduced into the vessel. Upon finishing the reaction, tea leaves were dried to get new black tea III.

An infusion extract obtained from the treated leaves for preparing a 0.1% by weight extract. It is found that the new black tea III contains 8% of theaflavins.

In view of the foregoing, it is clear that practice of the present invention will yield black tea, the use of which will yield a beverage of higher, beneficial polyphenol content. This, in turn, represents a "painless" source of chemorepressive and sunburn resistance substances for consumption by consumers.

Although the invention has been described with reference to specific embodiments, this description is not meant to be construed in a limited sense. Various modifications of the disclosed embodiments, as well as alternative embodiments of the invention will become apparent to persons skilled in the art upon the reference to the description of the invention. It is, therefore, contemplated that the appended claims will cover such modifications that fall within the scope of the invention.

We claim:

1. An improved black tea produced through a process involving the steps of:

selecting a measure of tea leaves;

moistening surfaces of said tea leaves with an aqueous tyrosinase solution without immersing said tea leaves therein and only to a degree that substantially no free liquid of said aqueous tyrosinase solution remains after said moistening;

exposing said tea leaves, once moistened, to an oxidizing agent;

drying said tea leaves to derive black tea.

2. The black tea of claim 1 wherein the moisture content of said tea leaves after said moistening is no greater than approximately 40% of the weight of said tea leaves prior to said moistening.

3. The black tea of claim 1 wherein said oxidizing agent is an oxygen-containing gas.

4. The black tea of claim 2 wherein said oxidizing agent is an oxygen-containing gas.

5. The black tea of claim 1 wherein said exposing of said tea leaves, once moistened, to an oxidizing agent, occurs at between approximately 20° C. and 50° C.

6. The black tea of claim 2 wherein said exposing of said tea leaves, once moistened, to an oxidizing agent, occurs at between approximately 20° C. and 50° C.

* * * * *